United States Patent [19]

Yan

[11] Patent Number: 5,108,551
[45] Date of Patent: Apr. 28, 1992

[54] RECLAMATION OF ALKANOLAMINE SOLUTIONS

[75] Inventor: Tsoung Y. Yan, Philadelphia, Pa.

[73] Assignee: Mobil Oil Corporation, Fairfax, Va.

[21] Appl. No.: 628,975

[22] Filed: Dec. 17, 1990

[51] Int. Cl.$^5$ .................. C07C 215/12; B01D 3/10; B01D 53/14
[52] U.S. Cl. .......................................... 203/6; 203/28; 203/96; 423/228; 423/229; 564/497
[58] Field of Search ............... 208/236; 564/487, 497, 564/488, 489; 201/2.5; 203/28, 29, 6, 96; 210/766; 423/228, 229

[56] References Cited

U.S. PATENT DOCUMENTS

| | | | |
|---|---|---|---|
| 4,079,117 | 3/1978 | Butwell | 423/228 |
| 4,113,837 | 9/1978 | Kendall et al. | 423/226 |
| 4,343,777 | 8/1982 | Dannhorn et al. | 423/228 |
| 4,389,383 | 6/1983 | Sokolik, Jr. et al. | 423/243 |
| 4,514,379 | 4/1985 | Miller | 423/229 |
| 4,795,565 | 1/1989 | Yan | 210/669 |

FOREIGN PATENT DOCUMENTS 2113211 8/1983 United Kingdom .............. 564/497

OTHER PUBLICATIONS

Treybal, R. E. "Mass-Transfer Operations", New York:McGraw Hill (1955), pp. 291-293 and 310.
K. F. Butwell, D. J. Kubec and P. W. Sigmund, "Alkanolamine Treating", Hydrocarbon Processing, Mar., 1982.

Primary Examiner—Michael Lewis
Assistant Examiner—Peter T. DiMauro
Attorney, Agent, or Firm—Alexander J. McKillop; Charles J. Speciale; Robert B. Furr, Jr.

[57] ABSTRACT

The present invention provides a method for purifying alkanolamine solutions which have lost at least a portion of their acid gas sorption capacity due to degradation of the alkanolamine into heat stable salts. Particularly, it has been found that the alkanolamine solution may be rejuvenated by charging the solution to the feed zone of a distillation column reactor at temperatures above about 160° C. and pressure of less than about 2000 mm Hg.

17 Claims, 1 Drawing Sheet

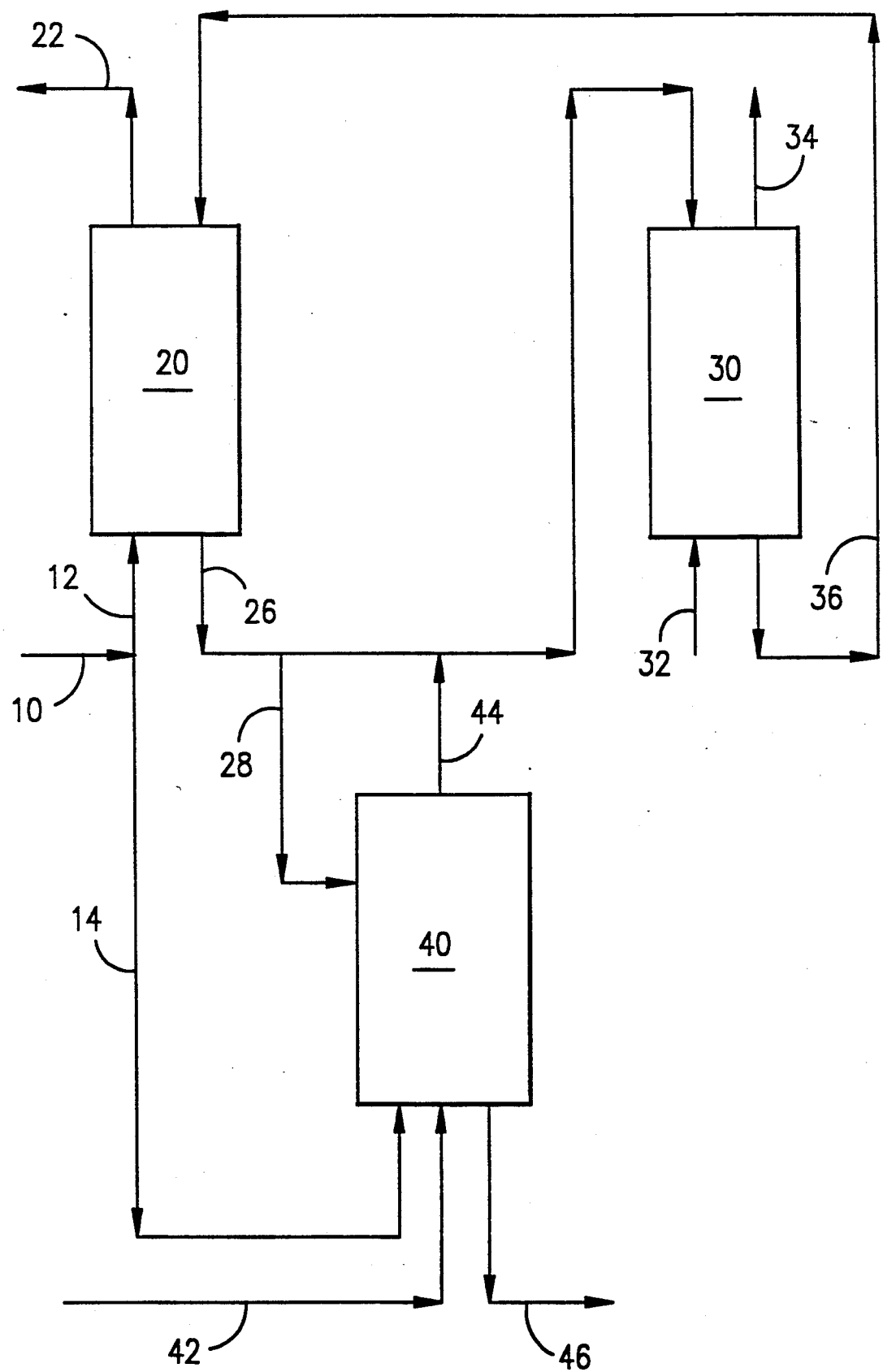

1

RECLAMATION OF ALKANOLAMINE SOLUTIONS

FIELD OF THE INVENTION

The present invention relates to the reclamation of alkanolamine solutions useful to sorb acid gas constituents from a gas stream. More specifically, the invention relates to a method for purifying and rejuvenating spent alkanolamine solutions to reduce corrosivity and to restore acid gas sorption capacity.

BACKGROUND OF THE INVENTION

Alkanolamine process units remove $H_2S$ and $CO_2$ from gaseous process streams, typically by countercurrently contacting an aqueous solution containing from about 20% to about 50% by weight of an alkanolamine with a gas stream containing $H_2S$ and/or $CO_2$.

Various amines, such as monoethanol amine (MEA), diethanol amine (DEA), and triethanolamine (TEA), merely to name a few, are useful in acid gas sorption. While each of these amines is an effective acid gas sorbent, sorption process conditions typically require the use of one or two selected alkanolamines due to the different boiling points of the various alkanolamines.

The removal of hydrogen sulfide from gaseous streams, such as the waste gases liberated in the course of various chemical and industrial processes, for example, in wood pulping, natural gas and crude oil production and in petroleum refining, has become increasingly important in combating atmospheric pollution. Hydrogen sulfide containing gases not only have an offensive odor, but such gases may cause damage to vegetation, painted surfaces and wildlife, and further may constitute a significant health hazard to humans. Government-wide regulations have increasingly imposed lower tolerances on the content of hydrogen sulfide which can be vented to the atmosphere, and it is now imperative in many localities to remove virtually all the hydrogen sulfide under the penalty of an absolute ban on continuing operation of a plant or the like which produces the hydrogen sulfide-containing gaseous stream. Solutions of water and one or more the alkanolamines are widely used in industry to remove hydrogen sulfide and carbon dioxide from such gaseous streams.

Corrosion in alkanolamine units significantly increases both operating and maintenance costs. The mechanisms of corrosive attack include general corrosive thinning, pitting corrosion-erosion, and stress-corrosion cracking. Corrosion control techniques include the use of more expensive corrosion and erosion resistant alloys, continuous or periodic removal of corrosion-promoting agents in suspended solids by filtration, activated carbon adsorption, or by the addition of corrosion inhibitors. (See Kohl, A. L. and Reisenfeld, F. C., *Gas Purification*, Gulf Publishing Company, Houston, 1979, pp. 91–105, as well as K. F. Butwell, D. J. Kubec and P. W. Sigmund, "Alkanolamine Treating", *Hydrocarbon Processing*, March, 1982.)

Further, it has been found that the acid gas sorption capacity in a circulating alkanolamine-water system decreases with time on stream in the absence of added makeup alkanolamine. This performance degradation has been found to be attributable to the accumulation of heat stable salts and complex amine degradation products. U.S. Pat. No. 4,795,565 to Yan describes a process for removing heat stable salts from an ethanolamine system by the use of ion exchange resins. The disclosure of U.S. Pat. No. 4,795,565 to Yan is incorporated herein by reference for the operating details both of an ethanolamine acid gas sorption system as well as for the heat stable salt removal process.

Heat stable salts may also be removed from certain aqueous alkanolamine systems by distillation. However, such separation has been limited in the past to relatively mild conditions of temperature and pressure to avoid thermal degradation of the alkanolamine. For example, while distillation effectively purifies monoethanol amine (MEA), fractionation of the higher boiling alkanolamines is complicated by their tendency to thermally degrade at elevated temperature. Diethanolamine (DEA), for example, boils at 268° C. at 760 mm Hg pressure and tends to oxidize and decompose at high temperature.

U.S. Pat. No. 4,079,117 to Butwell teaches a continuous process for removing acid gases, for example, carbon dioxide, from a hydrocarbon gas containing the same. Stripping and absorption temperatures in the Butwell process are maintained at below about 150° C.

U.S. Pat. No. 4,133,837 to Kendall et al. teaches a process for removing polymer from aqueous alkanolamine solutions which process includes the steps of adjusting the solution pH and removing the polymer by decantation and/or filtration.

U.S. Pat. No. 4,343,777 to Dannhorn et al. also relates to a process for removing accumulated polymer from an aqueous alkanolamine solution used for sorbing acid gases such as $CO_2$ and $H_2S$. After the spent alkanolamine solution is stripped of acid gas, the alkanolamine solution is contacted with a water immiscible organic solvent to extract the accumulated polymeric materials from the solution.

The chemistry of alkanolamine degradation is discussed in the Butwell et al. article cited above. Briefly, the Butwell et al. article notes that monoethanolamine (MEA) irreversibly degrades to N-(2-hydroxyethyl) ethylene diamine (HEED). HEED shows reduced acid gas removal properties and becomes corrosive at concentrations of at least about 0.4% by weight.

Diglycolamine (DGA), on the other hand, is said to produce a degradation product upon reaction with $CO_2$ which exhibits different properties. DGA is a registered trademark of Texaco, Inc. which identifies an amine having the chemical formula $NH_2$—$C_2H_4$—O—$C_2H_4$—OH. DGA degrades in the presence of $CO_2$ to form N,N'-bis(hydroxyethoxyethyl) urea (BHEEU) which is similar to HEED in corrosivity but differs in that BHEEU has no acid gas removal properties.

Diethanolamine (DEA) reacts with $CO_2$ to form N,N'-di(2-hydroxyethyl) piperazine. Unlike HEED and BHEEU, the piperazine compound is noncorrosive and has acid gas removal properties essentially equal to its parent, DEA. See the Butwell et al. article at page 113.

Diisopropylamine (DIPA) readily degrades in the contact with $CO_2$ to form 3-(2-hydroxypropyl) 5-methyl oxazolidone which shows essentially no acid gas removal properties. See the Butwell et al. article at page 113.

Numerous degradation products formed by the reaction of $H_2S$, or a mixture of $H_2S$ and $CO_2$ with diethanolamine have been reported from analyses of operating diethanolamine acid gas sorption processes and are shown below in Table 1.

TABLE 1

COMPOUNDS RESULTING FROM DEA DEGRADATION

| Name | Abbreviation | Structural formula |
|---|---|---|
| N,N-Bis (2-hydroxyethyl) piperazine | HEP | $HO-CH_2-CH_2-N(CH_2-CH_2)(CH_2-CH_2)N-CH_2-CH_2-OH$ |
| N,N,N-tris (2-hydroxyethyl) ethylenediamine | THEED | $(HO-CH_2-CH_2)_2N-CH_2-CH_2-NH-CH_2-CH_2-OH$ |
| Hydroxyethyl imidazolidone | HEI | cyclic: $CH_2-CH_2-N(CH_2-CH_2-OH)-C(=O)-N-CH_2$ (ring) |
| N-Methyldiethanolamine | MDEA | $(HO-CH_2-CH_2)_2N-CH_3$ |
| Oxazolidone | OZO | cyclic: $CH_2-CH_2-O-C(=O)-NH$ (ring) |
| Aminoethylethanolamine | AEEA | $NH_2-CH_2-CH_2-NH-CH_2-CH_2-OH$ |
| Bis-(2-hydroxy ethyl) glycine | BHG | $(HO-CH_2-CH_2)_2N-CH_2-C(=O)-OH$ |

Accumulation of these and other degradation products in the alkanolamine system reduces acid gas sorption capacity and increases the corrosivity of the alkanolamine solution. Previous processes have addressed removal of heat stable salts and amine degradation product, but such removal necessarily generates a waste stream, and the degraded alkanolamine withdrawn from the system must be replaced with fresh makeup alkanolamine. Thus is would be desirable to provide a method for restoring acid gas sorption capacity to a spent alkanolamine solution while minimizing the quantity of waste material withdrawn from the process. Further, it would be beneficial if a process for restoring alkanolamine acid gas sorption capacity would promote rejection of heat stable salts from the alkanolamine solution.

SUMMARY OF THE INVENTION

The invention provides a method for rejuvenating a spent alkanolamine solution which has lost at least a portion of its theoretical acid gas sorption capacity comprising the steps of:

(a) flowing said used alkanolamine solution to a distillation column reactor into a feed zone, wherein said feed zone is maintained at temperature above about 160° C. and wherein said distillation column reactor is maintained at low pressure, preferably not exceeding atmospheric pressure, more preferably at subatmospheric pressure;

(b) controlling reaction severity including temperature and residence time of said spent alkanolamine solution in said feed zone to evolve a distillable product mixture having a greater affinity for acid gas sorption than said spent alkanolamine solution;

(c) fractionating said distillable product mixture within said distillation column reactor;

(d) withdrawing a rejuvenated alkanolamine solution from said distillation column reactor at a point above said feed zone; and (e) withdrawing a stream containing rejected residue including heat stable salts from said distillation column reactor at a point below said feed zone.

The invention further provides, in a second aspect, a method for restoring acid gas sorption capacity to a spent alkanolamine solution comprising the steps of:

(a) flowing said spent alkanolamine solution to a distillation column reactor into a feed zone;

(b) heating said spent alkanolamine solution within said feed zone to a temperature above about 160° C. for a period of time at least sufficient to convert alkanolamine degradation products contained in said spent alkanolamine solution to their corresponding precursor alkanolamines;

(c) withdrawing alkanolamine from said feed zone and flowing said alkanolamine upwardly through said distillation column reactor to cool said withdrawn alkanolamine solution to a temperature below said feed zone temperature;

(d) withdrawing a rejuvenated alkanolamine solution from said distillation column reactor at a point above said feed zone; and (e) withdrawing a stream containing rejected residue including heat stable salts from said distillation column reactor at a point below said feed zone.

The invention still further comprises a method for restoring acid gas sorption capacity to a spent alkanolamine solution comprising the steps of:

(a) flowing said spent alkanolamine solution to a distillation column reactor into a feed zone;

(b) heating said spent alkanolamine solution within said feed zone to a temperature above about 160° C. at pressure of less than 150 mm Hg for a period of time at least sufficient to convert alkanolamine degradation products contained in said spent alkanolamine solution to their corresponding precursor alkanolamines;

(c) introducing stripping steam to said distillation column reactor at a point below said feed zone and flowing said stripping steam upwardly through said distillation column reactor;

(d) withdrawing alkanolamine from said feed zone, flowing said alkanolamine upwardly through said distillation column reactor, and cooling said withdrawn alkanolamine solution to a temperature below said feed zone temperature wherein the rates of alkanolamine withdrawal and the temperature gradient across the length of said distillation column reactor avoid substantial thermal degradation of said alkanolamine;

(e) withdrawing a rejuvenated alkanolamine solution from said distillation column reactor at a point above said feed zone, said withdrawn rejuvenated alkanolamine solution characterized by an AACI exceeding that of said spent alkanolamine solution; and (f) withdrawing a stream containing rejected residue including heat stable salts from said distillation column reactor at a point below said feed zone.

BRIEF DESCRIPTION OF THE DRAWING

The FIGURE is a simplified block diagram showing the major processing steps of the present invention.

DETAILED DESCRIPTION

The alkanolamine solution regeneration procedure of the present invention may be conducted in a batch or continuous mode. The continuous mode is preferred, and it is still more preferred to continuously reclaim a slipstream of acid-gas enriched alkanolamine solution comprising from about 1 to about 50% of the total alkanolamine stream by weight, preferably from about 2 to about 20% of the total alkanolamine stream by weight. The relative flow of the slipstream depends on degradation in the acid gas sorption system as well as the allowable level of alkanolamine degradation products in the system. The term "rich alkanolamine" as used herein refers to an aqueous alkanolamine solution which has contacted an acid gas-containing stream under suitable sorption conditions, and which has not been stripped of acid gas. For example, the aqueous diethanolamine (DEA) stream withdrawn from the DEA absorber tower of an operating commercial DEA deacidification process is a rich alkanolamine stream.

Alkanolamine Distillation Conditions

The distillation process of the present invention may be conducted in any suitable vacuum distillation apparatus, nonlimiting examples of which include columns containing either perforated trays, a packed bed, or a combination of both.

TABLE 2

| Distillation Column Reactor Conditions | | |
|---|---|---|
| Process Variable | Broad | Preferred |
| Overhead Temperature, °C. | 100–260 | 150–250 |
| Feed Zone Temperature, °C. | 150–550 | 160–500 |
| Bottom Temperature, °C. | 160–550 | 160–450 |
| Pressure, mm Hg | <2000 | <760 |
| Reflux Ratio, mol/mol | 0–10 | 0–5 |
| Steam Rate, Equivalent. volume water per volume DEA | 0.01–10 | 1–5 |
| Acid Gas Charge rate vol/vol DEA | 0.0001–0.01 | 0.0005–0.005 |
| Residence time of DEA solution in distillation column reactor, hrs. | 0.01–10 | 0.5–2 |

The units "Equivalent volume water per volume DEA" as used in Table 2 describe steam charge rate to the distillation zone in terms of the volume of liquid water under saturation conditions which must be vaporized to produce the required quantity of steam.

Steam injection to the distillation zone is not required to effect the desired alkanolamine purification, but beneficially lowers the required overhead temperature. Thus process operation with stripping steam is preferred. Low pressures within the distillation zone are preferred, with pressures below about 150 mm Hg being more preferred, and pressures below about 30 mm Hg being most preferred.

Rich DEA is a preferred reclamation feedstream because it has been surprisingly found that acid gases such as $H_2S$ and $CO_2$ suppress thermal degradation of diethanolamine under elevated temperatures within the feed zone. For this reason, it is particularly preferred to treat either a rich alkanolamine stream, a mixture of rich and lean alkanolamine streams, or to charge a small amount of acid gas such as $H_2S$ and $CO_2$ to the distillation column reactor. A rich DEA stream requires less supplemental crude gas to meet the minimum required acid gas partial pressure for suppressing alkanolamine degradation within the distillation zone. Typical acid gas enriched alkanolamine solutions withdrawn from operating industrial acid gas sorption processes can be reasonably expected to contain acid gas concentrations sufficient to achieve the desired suppression.

The rejuvenation reaction within the feed zone is preferably carried out under conditions of minimum residence time, with the maximum charge rate limited by the available heat input and by fluid dynamics of the particular distillation tower reactor. Thus the spent alkanolamine charge rate to the distillation column reactor is preferably as high as possible while meeting the minimum feed zone temperature requirement without flooding the column. Most preferably, the spent alkanolamine solution rises to reaction temperature within the feed zone almost instantaneously, and the resulting alkanolamine reaction products are then withdrawn from the feed zone as quickly as possible to be cooled as they flow upwardly through the distillation column reactor.

Referring now to the FIGURE, a crude gas 10 containing $H_2S$ and $CO_2$ is split to form a DEA absorber crude gas feedstream 12 and a DEA reclamation slipstream 14. The DEA absorber crude gas feedstream 12 enters a lower section of DEA absorber 20 and flows upwardly, countercurrently contacting lean DEA flowing downwardly through the DEA absorber 20. The lean DEA 36 flows continuously to DEA absorber 20 from DEA stripper 30, described in greater detail below.

Rich DEA 26 containing sorbed acid gases is withdrawn from a lower section of DEA absorber 20 and is charged to an upper section of DEA stripper 30 and flows downwardly as it is countercurrently stripped with an inert gas such as steam. If steam is used as the stripping medium, the stripping temperature is suitably about 116° C. (240° F.). A stream enriched in stripping gas and the stripped acid gases 34 is then withdrawn from an upper section of DEA stripper 30. The lean DEA solution is continuously withdrawn from a lower section of DEA stripper 30 and recycled to an upper section of DEA absorber 20.

A fraction, typically from about 1 to about 50 percent, of the rich DEA flowing from the DEA absorber to the DEA stripper is diverted to form a slipstream 28 and is charged to vacuum distillation reactor column 40.

A crude gas sidestream 14 may optionally be charged to vacuum distillation reactor column 40, preferably to a lower section of the vacuum distillation reactor column, to maintain concentration/partial pressure within the range shown above in Table 2. Stripping steam 42 is charged to a lower section of vacuum distillation reactor column 40. The purified DEA 44 solution is withdrawn from vacuum distillation reactor column 40 through line 44 and returns to line 26 which conveys the purified DEA solution enriched in acid gases to DEA stripper 30 where the solution is stripped of acid gases as described above. The bottom stream withdrawn from vacuum distillation reactor column 40, which is enriched in DEA degradation products, particularly heat stable salts is withdrawn from the process unit and routed to suitable disposal facilities (not shown) in accordance with applicable safety and environmental regulations.

EXAMPLES

An aqueous diethanolamine (DEA) solution containing about 20% by weight DEA, 30% by weight other organics including DEA degradation products, and about 0.1% by weight total residual $H_2S$ and $CO_2$ was charged at a rate of about 50 cc/hr to the feed zone of a 1 inch I.D. by 30 inch long stainless steel distillation column reactor containing stainless steel packing. To add supplemental $H_2S$ in the most convenient manner in Examples 2 and 3, about 10% by weight of the aqueous DEA solution was saturated with $H_2S$, and then admixed with the remaining 90% by weight to provide a feedstream containing 90% lean DEA and 10% $H_2S$-saturated DEA. The feed zone, midpoint, and overhead temperatures are shown below in Tables 3, 4, and 5. The overhead and bottom liquids were collected and analyzed. Surprisingly, the overhead product from the distillative reaction column contained more DEA than the spent DEA feed. Results for three experimental runs, Examples 1, 2, and 3, are shown below in Tables 3, 4, and 5, respectively.

TABLE 3

EXAMPLE 1
Distillation Column Conditions - EXAMPLE 1
Column Top Temperature, °C. 191
Feed Zone Temperature, °C. 120
Midpoint Temperature, °C. 219
Pressure, mm Hg 21

|  | Feed, g. | Overhead Product, g. | Bottom Product, g. | Net Change |
|---|---|---|---|---|
| DEA | 16.71 | 26.77 | 1.77 | +11.83 |

TABLE 3-continued

EXAMPLE 1
Distillation Column Conditions - EXAMPLE 1
Column Top Temperature, °C. 191
Feed Zone Temperature, °C. 120
Midpoint Temperature, °C. 219
Pressure, mm Hg 21

|  | Feed, g. | Overhead Product, g. | Bottom Product, g. | Net Change |
|---|---|---|---|---|
| BHEP | 9.14 | 1.98 | 1.33 | −5.83 |
| NTO | 30.24 | 6.37 | 2.58 | −21.29 |
| H2O | 23.90 | 35.69 | 2.42 | +14.21 |
| HSS | 39.38 | 8.35 | 3.91 | −27.12 |
| AACI | 21.26 | 27.76 | 2.44 | — |
| Relative AACI | 1.0 | 1.31 | — | — |

TABLE 4

EXAMPLE 2
Distillation Column Conditions - EXAMPLE 2
Column Top Temperature, °C. 184
Feed Zone Temperature, °C. 170
Midpoint Temperature, °C. 219
Pressure, mm Hg 21

|  | Feed, g. | Overhead Product, g. | Bottom Product, g. | Net Change |
|---|---|---|---|---|
| DEA | 18.17 | 26.78 | 4.44 | +13.05 |
| BHEP | 9.94 | 2.12 | 2.66 | −5.16 |
| NTO | 26.00 | 9.71 | 0.80 | −15.49 |
| H2O | 32.89 | 37.24 | 3.40 | +7.75 |
| HSS | 35.94 | 11.83 | 3.46 | −20.65 |
| AACI | 23.14 | 27.84 | — | — |
| Relative AACI | 1.0 | 1.20 | — | — |

TABLE 5

EXAMPLE 3
Distillation Column Conditions - EXAMPLE 3
Column Top Temperature, °C. 199
Feed Zone Temperature, °C. 132
Midpoint Temperature, °C. 241
Pressure, mm Hg 21

|  | Feed, g. | Overhead Product, g. | Bottom Product, g. | Net Change |
|---|---|---|---|---|
| DEA | 20.05 | 34.17 | 4.97 | +19.09 |
| BHEP | 10.97 | 3.11 | 1.03 | −6.83 |
| NTO | 28.68 | 6.17 | 1.97 | −20.54 |
| H2O | 36.29 | 38.85 | 4.10 | +6.66 |
| HSS | 39.65 | 9.28 | 3.00 | −27.37 |
| AACI | 25.54 | 35.73 | 5.49 | — |
| Relative AACI | 1.0 | 1.40 | — | — |

As used in Table 3, DEA designates diethanolamine, BHEP is structurally defined above in Table 1 NTO designates non-titratable organics, HSS designates heat-stable salts, and AACI designates the acid absorption capacity index, which is defined as the sum of the sum of the weight percent DEA and one-half (½) the weight percent BHEP.

Changes and modifications in the specifically described embodiments can be carried out without departing from the scope of the invention which is intended to be limited only by the scope of the appended claims.

What is claimed is:

1. A method for rejuvenating a spent alkanolamine solution which has lost at least a portion of its theoretical acid gas sorption capacity comprising the steps of:
 (a) flowing said spent alkanolamine solution to a distillation column reactor into a feed zone, wherein said feed zone is maintained at temperature above about 160° C. and wherein said distillation column reactor is maintained at pressure below about 2000 mm Hg;

(b) charging acid gas selected from the group consisting of $H_2S$ and $CO_2$ to said distillation column reactor;

(c) controlling residence time of said spent alkanolamine solution in said distillation column reactor to at least partially convert said spent alkanolamine solution to a distillable product mixture having a greater affinity for acid gas sorption than said spent alkanolamine solution;

(d) fractionating said distillable product mixture within said distillation column reactor;

(e) withdrawing a rejuvenated alkanolamine solution from said distillation column reactor at a point above said feed zone; and (f) withdrawing a stream containing rejected residue including heat stable salts from said distillation column reactor at a point below said feed zone.

2. The method of claim 1 further comprising introducing steam to said distillation column reactor at a point below said feed zone.

3. The method of claim 2 wherein said steam is introduced to said alkanolamine solution and charged to said distillation column reactor in volume ratios of steam:spent alkanolamine charge of from about 0.01 to about 10.

4. The method of claim 1 further comprising controlling pressure within said distillation column reactor at less than about 760 mm Hg.

5. The method of claim 4 wherein pressure within said distillation column reactor is less than about 150 mm Hg.

6. The method of claim 1 wherein the mass flowrate of DEA withdrawn in said rejuvenated alkanolamine solution exceeds the mass flowrate of DEA charged to said distillation column reactor.

7. A method for restoring acid gas sorption capacity to a spent alkanolamine solution comprising the steps of:

(a) flowing said spent alkanolamine solution to a distillation column reactor into a feed zone;

(b) charging acid gas selected from the group consisting of $H_2S$ and $CO_2$ to said distillation column reactor;

(c) heating said spent alkanolamine solution within said feed zone to a temperature above about 160° C. for a period of time at least sufficient to convert alkanolamine degradation products contained in said spent alkanolamine solution to their corresponding precursor alkanolamines;

(d) withdrawing alkanolamine from said feed zone and flowing said alkanolamine upwardly through said distillation column reactor to cool said withdrawn alkanolamine solution to a temperature below said feed zone temperature;

(e) withdrawing a rejuvenated alkanolamine solution from said distillation column reactor at a point above said feed zone; and (f) withdrawing a stream containing rejected residue including heat stable salts from said distillation column reactor at a point below said feed zone.

8. The method of claim 7 further comprising introducing steam to said distillation column reactor at a point below said feed zone.

9. The method of claim 6 wherein said steam is introduced to said alkanolamine solution and charged to said distillation column reactor in volume ratios of steam:spent alkanolamine charge of from about 0.01 to about 10.

10. The method of claim 7 further comprising controlling pressure within said distillation column reactor at less than about 150 mm Hg.

11. The method of claim 10 wherein pressure within said distillation column reactor is less than about 30 mm Hg.

12. The method of claim 7 wherein the mass flowrate of DEA withdrawn in said rejuvenated alkanolamine solution exceeds the mass flowrate of DEA charged to said distillation column reactor.

13. A method for restoring acid gas sorption capacity to a spent alkanolamine solution comprising the steps of:

(a) flowing said spent alkanolamine solution to a distillation column reactor into a feed zone;

(b) charging acid gas selected from the group consisting of $H_2S$ and $CO_2$ to said distillation column reactor;

(c) heating said spent alkanolamine solution within said feed zone to a temperature above about 160° C. at pressure of less than 2000 mm Hg for a period of time at least sufficient to convert alkanolamine degradation products contained in said spent alkanolamine solution to their corresponding precursor alkanolamines;

(d) introducing stripping steam to said distillation column reactor at a point below said feed zone and flowing said stripping steam upwardly through said distillation column reactor;

(e) withdrawing alkanolamine from said feed zone, flowing said alkanolamine upwardly through said distillation column reactor, and cooling said withdrawn alkanolamine solution to a temperature below said feed zone temperature wherein the rates of alkanolamine withdrawal and the temperature gradient across the length of said distillation column reactor avoid substantial thermal degradation of said alkanolamine;

(f) withdrawing a rejuvenated alkanolamine solution from said distillation column reactor at a point above said feed zone, said withdrawn rejuvenated alkanolamine solution characterized by an AACI exceeding that of said spent alkanolamine solution; and (g) withdrawing a stream containing heat stable salts from said distillation column reactor at a point below said feed zone.

14. The method of claim 13 wherein said steam is introduced to said alkanolamine solution and charged to said distillation column reactor in volume ratios of steam:spent alkanolamine charge of from about 0.01 to about 10.

15. The method of claim 13 further comprising controlling pressure within said distillation column reactor at less than about 760 mm Hg.

16. The method of claim 15 wherein pressure within said distillation column reactor is less than about 150 mm Hg.

17. The method of claim 13 wherein the mass flowrate of DEA withdrawn in said rejuvenated alkanolamine solution exceeds the mass flowrate of DEA charged to said distillation column reactor.

* * * * *